US009393423B2

(12) United States Patent
Parramon et al.

(10) Patent No.: US 9,393,423 B2
(45) Date of Patent: *Jul. 19, 2016

(54) FRACTIONALIZED STIMULATION PULSES IN AN IMPLANTABLE STIMULATOR DEVICE

(71) Applicant: Boston Scientific Neuromodulation Corporation, Valencia, CA (US)

(72) Inventors: Jordi Parramon, Valencia, CA (US); Rafael Carbunaru, Valley Village, CA (US); Matt I. Haller, Valley Village, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/329,608

(22) Filed: Jul. 11, 2014

(65) Prior Publication Data

US 2014/0336726 A1    Nov. 13, 2014

Related U.S. Application Data

(63) Continuation of application No. 12/824,663, filed on Jun. 28, 2010, now Pat. No. 8,812,131, which is a continuation of application No. 12/121,281, filed on May 15, 2008, now Pat. No. 7,890,182.

(51) Int. Cl.
*A61N 1/36* (2006.01)
*A61N 1/372* (2006.01)
*A61N 1/05* (2006.01)

(52) U.S. Cl.
CPC .............. *A61N 1/36178* (2013.01); *A61N 1/05* (2013.01); *A61N 1/36* (2013.01); *A61N 1/36071* (2013.01);

(Continued)

(58) Field of Classification Search
USPC ............................................... 607/70
See application file for complete search history.

(56) References Cited

U.S. PATENT DOCUMENTS 3,646,940 A    3/1972 Timm et al.
3,727,616 A    4/1973 Lenzkes
(Continued)

FOREIGN PATENT DOCUMENTS

CN    101239222 A    8/2008
GB       2449546 A    11/2008
(Continued)

OTHER PUBLICATIONS

U.S. Appl. No. 60/985,353, filed Nov. 5, 2007, Fang et al.
(Continued)

*Primary Examiner* — Kennedy Schaetzle
(74) *Attorney, Agent, or Firm* — Lewis, Reese & Nesmith, PLLC

(57) ABSTRACT

A method for configuring stimulation pulses in an implantable stimulator device having a plurality of electrodes is disclosed, which method is particularly useful in adjusting the electrodes by current steering during initialization of the device. In one aspect, a set of ideal pulses for patient therapy is determined, in which at least two of the ideal pulses are of the same polarity and are intended to be simultaneous applied to corresponding electrodes on the implantable stimulator device during an initial duration. These pulses are reconstructed into fractionalized pulses, each comprised of pulse portions. The fractionalized pulses are applied to the corresponding electrodes on the device during a final duration, but the pulse portions of the fractionalized pulses are not simultaneously applied during the final duration.

36 Claims, 11 Drawing Sheets

(52) U.S. Cl.
CPC ........ *A61N 1/36171* (2013.01); *A61N 1/36175* (2013.01); *A61N 1/37235* (2013.01); *A61N 1/0551* (2013.01)

(56) References Cited

U.S. PATENT DOCUMENTS

| | | | |
|---|---|---|---|
| 3,822,708 A | | 7/1974 | Zilber |
| 4,177,819 A * | | 12/1979 | Kofsky et al. ............ 607/63 |
| 4,408,608 A | | 10/1983 | Daly et al. |
| 4,520,825 A | | 6/1985 | Thompson et al. |
| 4,535,777 A * | | 8/1985 | Castel ...................... 607/71 |
| 4,608,985 A | | 9/1986 | Crish et al. |
| 4,649,936 A | | 3/1987 | Ungar et al. |
| 4,702,254 A | | 10/1987 | Zabara |
| 5,007,902 A | | 4/1991 | Witt |
| 5,119,832 A | | 6/1992 | Xavier |
| 5,188,104 A | | 2/1993 | Wernicke et al. |
| 5,199,430 A | | 4/1993 | Fang et al. |
| 5,562,717 A | | 10/1996 | Tippey et al. |
| 5,601,617 A | | 2/1997 | Loeb et al. |
| 5,700,282 A | | 12/1997 | Zabara |
| 5,776,170 A | | 7/1998 | MacDonald et al. |
| 5,983,141 A | | 11/1999 | Sluijter et al. |
| 6,002,964 A | | 12/1999 | Feler et al. |
| 6,052,624 A | | 4/2000 | Mann |
| 6,161,048 A | | 12/2000 | Sluijter et al. |
| 6,178,351 B1 | | 1/2001 | Mower |
| 6,185,452 B1 | | 2/2001 | Schulman et al. |
| 6,246,912 B1 | | 6/2001 | Sluijter et al. |
| 6,298,256 B1 | | 10/2001 | Meyer |
| 6,325,764 B1 | | 12/2001 | Griffith et al. |
| 6,393,325 B1 | | 5/2002 | Mann et al. |
| 6,516,227 B1 | | 2/2003 | Meadows et al. |
| 6,587,724 B2 | | 7/2003 | Mann |
| 6,600,954 B2 | | 7/2003 | Cohen et al. |
| 6,609,032 B1 | | 8/2003 | Woods et al. |
| 6,615,084 B1 | | 9/2003 | Cigaina |
| 6,684,105 B2 | | 1/2004 | Cohen et al. |
| 6,712,753 B2 | | 3/2004 | Manne |
| 6,731,986 B2 | | 5/2004 | Mann |
| 6,775,148 B2 | | 8/2004 | Hong |
| 6,839,594 B2 | | 1/2005 | Cohen et al. |
| 6,849,073 B2 | | 2/2005 | Hoey et al. |
| 6,895,280 B2 | | 5/2005 | Meadows et al. |
| 6,909,917 B2 | | 6/2005 | Woods et al. |
| 6,928,320 B2 | | 8/2005 | King |
| 6,978,180 B2 | | 12/2005 | Tadlock |
| 7,054,686 B2 | | 5/2006 | MacDonald |
| 7,054,689 B1 | | 5/2006 | Whitehurst et al. |
| 7,146,223 B1 | | 12/2006 | King |
| 7,174,215 B2 | | 2/2007 | Bradley |
| 7,177,690 B2 | | 2/2007 | Woods et al. |
| 7,180,760 B2 | | 2/2007 | Varrichio et al. |
| 7,184,837 B2 | | 2/2007 | Goetz |
| 7,203,548 B2 | | 4/2007 | Whitehurst et al. |
| 7,212,133 B2 | | 5/2007 | Goetze et al. |
| 7,212,865 B2 | | 5/2007 | Cory |
| 7,239,926 B2 | | 7/2007 | Goetz |
| 7,247,155 B2 | | 7/2007 | Hoey et al. |
| 7,252,090 B2 | | 8/2007 | Goetz |
| 7,263,402 B2 | | 8/2007 | Thacker et al. |
| 7,292,890 B2 | | 11/2007 | Whitehurst et al. |
| 7,317,945 B2 | | 1/2008 | Litvak et al. |
| 7,389,145 B2 | | 6/2008 | Kilgore et al. |
| 7,450,987 B2 | | 11/2008 | Varrichio et al. |
| 7,496,404 B2 | | 2/2009 | Meadows et al. |
| 7,519,431 B2 | | 4/2009 | Goetz et al. |
| 7,526,341 B2 | | 4/2009 | Goetz et al. |
| 7,571,007 B2 | | 8/2009 | Erickson |
| 7,603,174 B2 | | 10/2009 | De Ridder |
| 7,613,519 B2 | | 11/2009 | De Ridder |
| 7,613,520 B2 | | 11/2009 | De Ridder |
| 7,676,273 B2 | | 3/2010 | Goetz et al. |
| 7,734,340 B2 | | 6/2010 | De Ridder |
| 7,742,819 B2 | | 6/2010 | Moffitt |
| 7,769,462 B2 * | | 8/2010 | Meadows et al. ........ 607/46 |
| 7,805,197 B2 * | | 9/2010 | Bradley ................... 607/46 |
| 7,860,570 B2 | | 12/2010 | Whitehurst et al. |
| 7,890,182 B2 | | 2/2011 | Parramon et al. |
| 7,890,185 B2 | | 2/2011 | Cohen et al. |
| 8,027,718 B2 | | 9/2011 | Spinner et al. |
| 8,060,208 B2 | | 11/2011 | Kilgore et al. |
| 8,224,453 B2 | | 7/2012 | De Ridder |
| 8,280,515 B2 | | 10/2012 | Greenspan |
| 8,340,775 B1 | | 12/2012 | Cullen et al. |
| 8,364,271 B2 | | 1/2013 | De Ridder |
| 8,364,273 B2 | | 1/2013 | DeRidder |
| 8,401,655 B2 | | 3/2013 | DeRidder |
| 8,423,147 B2 | | 4/2013 | Alataris et al. |
| 8,428,748 B2 | | 4/2013 | Alataris et al. |
| 8,433,418 B2 | | 4/2013 | De Ridder |
| 8,612,018 B2 | | 12/2013 | Gillbe |
| 8,712,533 B2 | | 4/2014 | Alataris et al. |
| 8,788,044 B2 | | 7/2014 | John |
| 8,825,166 B2 | | 9/2014 | John |
| 8,977,363 B2 | | 3/2015 | Carroll et al. |
| 2002/0055779 A1 | | 5/2002 | Andrews |
| 2004/0015205 A1 | | 1/2004 | Whitehurst et al. |
| 2004/0049231 A1 | | 3/2004 | Hafer |
| 2004/0158304 A1 | | 8/2004 | Cory et al. |
| 2004/0167583 A1 | | 8/2004 | Knudson et al. |
| 2004/0167584 A1 | | 8/2004 | Carroll et al. |
| 2004/0172085 A1 | | 9/2004 | Knudson et al. |
| 2004/0172086 A1 | | 9/2004 | Knudson et al. |
| 2004/0172088 A1 | | 9/2004 | Knudson et al. |
| 2004/0176812 A1 | | 9/2004 | Knudson et al. |
| 2004/0193230 A1 | | 9/2004 | Overstreet et al. |
| 2004/0210270 A1 | | 10/2004 | Erickson |
| 2004/0210271 A1 | | 10/2004 | Campen et al. |
| 2005/0038484 A1 | | 2/2005 | Knudson et al. |
| 2005/0065575 A1 | | 3/2005 | Dobak |
| 2005/0143781 A1 | | 6/2005 | Carbunaru et al. |
| 2005/0149148 A1 | | 7/2005 | King |
| 2005/0203588 A1 | | 9/2005 | King |
| 2005/0209655 A1 | | 9/2005 | Bradley et al. |
| 2005/0245977 A1 | | 11/2005 | Varrichio et al. |
| 2005/0245987 A1 | | 11/2005 | Woods et al. |
| 2005/0245993 A1 | | 11/2005 | Varrichio et al. |
| 2005/0245994 A1 | | 11/2005 | Varrichio et al. |
| 2006/0004422 A1 | | 1/2006 | De Ridder |
| 2006/0009820 A1 | | 1/2006 | Royle |
| 2006/0015153 A1 | | 1/2006 | Gliner et al. |
| 2006/0025832 A1 | | 2/2006 | O'Keefe et al. |
| 2006/0030895 A1 | | 2/2006 | Simon et al. |
| 2006/0030899 A1 | | 2/2006 | O'Keefe et al. |
| 2006/0074456 A1 | | 4/2006 | Pyles et al. |
| 2006/0161236 A1 | | 7/2006 | King |
| 2006/0170486 A1 | | 8/2006 | Tranchina et al. |
| 2006/0195145 A1 | | 8/2006 | Lee et al. |
| 2006/0229687 A1 | | 10/2006 | Goetz et al. |
| 2007/0060954 A1 | | 3/2007 | Cameron et al. |
| 2007/0073354 A1 | | 3/2007 | Knudson et al. |
| 2007/0097719 A1 | | 5/2007 | Parramon et al. |
| 2007/0123953 A1 | | 5/2007 | Lee et al. |
| 2007/0150034 A1 | | 6/2007 | Rooney et al. |
| 2007/0156203 A1 | | 7/2007 | Varrichio et al. |
| 2007/0203538 A1 | | 8/2007 | Stone et al. |
| 2007/0203540 A1 | | 8/2007 | Goetz et al. |
| 2007/0203543 A1 | | 8/2007 | Stone et al. |
| 2007/0203546 A1 | | 8/2007 | Stone et al. |
| 2007/0213789 A1 | | 9/2007 | Nolan et al. |
| 2007/0213790 A1 | | 9/2007 | Nolan et al. |
| 2007/0239226 A1 | | 10/2007 | Overstreet |
| 2007/0239228 A1 * | | 10/2007 | Bradley ................... 607/59 |
| 2007/0244519 A1 | | 10/2007 | Keacher et al. |
| 2007/0245318 A1 | | 10/2007 | Goetz et al. |
| 2007/0265679 A1 | | 11/2007 | Bradley et al. |
| 2007/0276450 A1 | | 11/2007 | Meadows et al. |
| 2007/0293914 A1 | | 12/2007 | Woods et al. |
| 2007/0299482 A1 | | 12/2007 | Littlewood et al. |
| 2008/0004674 A1 | | 1/2008 | King et al. |
| 2008/0027514 A1 | | 1/2008 | DeMulling et al. |
| 2008/0033511 A1 | | 2/2008 | Dobak |
| 2008/0046036 A1 | | 2/2008 | King et al. |

(56) References Cited

U.S. PATENT DOCUMENTS

| | | |
|---|---|---|
| 2008/0058773 A1 | 3/2008 | John |
| 2008/0071325 A1 | 3/2008 | Bradley |
| 2008/0103552 A1 | 5/2008 | Goetz et al. |
| 2008/0215119 A1 | 9/2008 | Woods et al. |
| 2008/0221637 A1 | 9/2008 | Woods et al. |
| 2008/0228236 A1 | 9/2008 | Varrichio et al. |
| 2008/0234791 A1 | 9/2008 | Arle et al. |
| 2008/0288023 A1 | 11/2008 | John |
| 2009/0048643 A1 | 2/2009 | Erickson et al. |
| 2009/0204173 A1 | 8/2009 | Fang et al. |
| 2010/0137938 A1 | 6/2010 | Kishawi et al. |
| 2010/0152817 A1 | 6/2010 | Gillbe |
| 2010/0241190 A1 | 9/2010 | Kilgore et al. |
| 2010/0249875 A1 | 9/2010 | Kishawi et al. |
| 2011/0009919 A1 | 1/2011 | Carbunaru et al. |
| 2011/0184488 A1 | 7/2011 | De Ridder |
| 2012/0172946 A1 | 7/2012 | Alataris et al. |

FOREIGN PATENT DOCUMENTS

| | | |
|---|---|---|
| JP | S58-086177 | 5/1983 |
| WO | 01/43818 | 6/2001 |
| WO | 03/066154 A2 | 8/2003 |
| WO | 2004/007018 A1 | 1/2004 |
| WO | 2004/043537 | 5/2004 |
| WO | 2005/099813 | 10/2005 |
| WO | 2005/101627 | 10/2005 |
| WO | 2005/101660 | 10/2005 |
| WO | 2005/101661 | 10/2005 |
| WO | 2006/073393 | 7/2006 |
| WO | 2006/073405 | 7/2006 |
| WO | 2006/112852 | 10/2006 |
| WO | 2006/128037 | 11/2006 |
| WO | 2007/002741 | 1/2007 |
| WO | 2008/142402 A1 | 11/2008 |
| WO | 2009/061813 A1 | 5/2009 |
| WO | 2010/111358 A1 | 9/2010 |

OTHER PUBLICATIONS

U.S. Appl. No. 60/951,177, filed Jul. 20, 2007, Lee.
U.S. Appl. No. 60/685,036, filed May 25, 2005, Erickson et al.
Banazzour et al.; Reversal of Rigidity and Improvement in Motor Performance by Subthalamic High-frequency Stimulation in MPTP-treated Monkeys; (1992), European Journal of Neuroscience, vol. 5, pp. 382-389.
Beurrier et al., Subthalamic Stimulation Elicits Hemiballismus in Normal Monkey, NeuroReport, vol. 8, No. 7, May 6, 1997, pp. 1625-1629.
Beurrier et al., Subthalamic Nucleus Neurons Switch from Single-Spike Activity to Burst-Firing Mode; The Journal of Neuroscience, Jan. 15, 1999, 19(2):599-609.
Kilgore et al., Nerve Conduction Block Utilising High-frequency Alternating Current, Medical & Biological Engineering & Computing, 2004, vol. 42, pp. 394-406.
Nunemaker et al., A Tale of Two Rhythms: A Comparative Review of the Pulsatile Endocrine Systems Regulating insulin and GnRH Secretion, Department of Pharmacology and Toxicology, Virginia Commonwealth University, P. O. Box 980524, Richmond, VA 23298, Received Jul. 24, 2005 © Cellscience.
Urbain et al., The Switch of Subthalamic Neurons From an Irregular to a Bursting Pattern Does Not Soley Depend on Their GABAergic Inputs in the Anesthetic-Free Rat, The Journal of Neuroscience, Oct. 1, 2002, 22(19): pp. 8665-8675.
Geddes, Leslie A., Accuracy Limitations of Chronaxie Values, IEEE Transactions on Biomedical Engineering, vol. 51, No. 1, Jan. 2004, pp. 176-181.
Mateev et al.; "Implications of All-or-None Synaptic Transmission and Short-Term Depression beyond Vesicle Depletion: a Computational Study;" The Journal of Neuroscience. Feb. 15, 2000; pp. 1575-1588.
Mateev et al.; "Differential Short-term Synaptic Plasticity and Transmission of Complex Spike Trains to Depress or to Facilitate;" Cerebral Cortex; Nov. 2000; vol. 10 No. 11; pp. 1143-1153.
Munglani, Rajesh, "The Longer Term Effect of Pulsed Radiofrequency for Neuropathic Pain," International Association for the Study of Pain, pp. 437-439, 1999.
Sluijter, Menno E. et al., "The Effects of Pulsed Radiofrequency Fields Applied to the Dorsal Root Ganglion—A Preliminary Report," The Pain Clinic, vol. 11, No. 2, pp. 109-117, 1998.
"Analysis of Failed Spinal Cord Stimulation Trials in the Treatment of Intractable Chronic Pain," J. Korean Neurosurgery Society, vol. 43, 2008, pp. 85-89.
Barolat, Giancarlo, et al., "Multifactorial Analysis of Epidural Spinal Cord Stimulation," Stereotactic and Functional Neurosurgery, 56, 1991, pp. 77-103.
Bhadra, Narendra, et al., "High Frequency Electrical Conduction Block of the Pudendal Nerve," Journal of Neural Engineering, Institute of Physics Publishing, vol. 3, May 17, 2006, pp. 180-187.
Bhadra, Niloy, et al., "High-Frequency Electrical Conduction Block of Mammalian Peripheral Motor Nerve," Muscle & Nerve, 32, Dec. 2005, pp. 782-790.
Bhadra, Niloy, et al., "Simulation of High-Frequency Sinusoidal Electrical Block of Mammalian Myelinated Axons," Springer, J Comput Neurosci, Jan. 3, 2007, 22, pp. 313-326.
Boger, Adam, et al., "Bladder Voiding by Combined High Frequency Electrical Pudendal Nerve Block and Sacral Root Stimulation," Wiley Interscience, Neurourology and Urodynamics, 27, 2008, pp. 435-439.
Bowman, Bruce R., et al., "Response of Single Alpha Motoneurons to High-Frequency Pulse Trains," Appl. Neurophysial., 49, 1986, pp. 121-138.
Cahana, Alex, et al., "Acute Differential Modulation of Synaptic Transmission and Cell Survival During Exposure to Pulsed and Continuous Radiofrequency Energy," The Journal of Pain, vol. 4, No. 4, May 2003, pp. 197-202.
De Ridder, Dirk, et al., "Burst Spinal Cord Stimulation: Toward Paresthesia-Free Pain Suppression," Neurosurgery Online, vol. 66, No. 5, May 2010, pp. 986-990, obtained from <www.neurosurgery-online.com>.
Grill, Warren M., et al., "Stimulus Waveforms for Selective Neural Stimulation," IEEE Engineering in Medicine and Biology, Jul./Aug. 1995, pp. 375-385.
Higuchi, Yoshinori, M.D., et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, pp. 850-856.
Holsheimer, Jan, et al., "Effectiveness of Spinal Cord Stimulation in the Management of Chronic Pain: Analysis of Technical Drawbacks and Solutions," Neurosurgery, vol. 40, Issue 5, May 1997, Apr. 23, 2009, pp. 990-999, obtained from <http://journals.lww.com/neurosurgery/Fulltext/1997/05000/Effectiveness_of_Spinal_Cord_Stimulation_in_the.23.aspx>.
Hopp, F.A., et al., "Effect of Anodal Blockade of Myelinated Fibers on Vagal C-Fiber Afferents," The American Physiological Society, Apr. 21, 1980, pp. 454-462.
Huxley, A. F., "Excitation and Conduction in Nerve: Quantitative Analysis," Science, vol. 145, Sep. 11, 1964, pp. 1154-1159.
Kilgore, Kevin L., Ph.D., et al., "Reversible Nerve Conduction Block Using Kilohertz Frequency Alternating Current," Neuromodulation: Technology at the Neural Interface, International Neurmodulation Society, 17, 2014, pp. 242-255.
Kumar, Krishna, M.B.B.S., M.S., et al., "Spinal Cord Stimulation in Treatment of Chronic Benign Pain: Challengs in Treatment Planning and Present Status, a 22-Year Experience," Neurosurgery, vol. 58, No. 3, Mar. 2006, pp. 481-496.
Larson, Sanford J., M.D., Ph.D., et al., "Neurophysiological Effects of Dorsal col. Stimulation in Man and Monkey," Journal of Neurosurgery, vol. 41, Aug. 1974, pp. 217-223.
Linderoth, Bengt, M.D., Ph.D., et al., "Mechanisms of Spinal Cord Stimulation in Painful Syndromes: Role of Animal Models," American Academy of Pain Medicine, vol. 7, No. S1, 2006, pp. S14-S26.

(56) References Cited

OTHER PUBLICATIONS

Linderoth, Bengt, M.D., Ph.D., et al., "Physiology of Spinal Cord Stimulation: Review and Update," International Neuromodulation Society, Neuromodulation, vol. 2, No. 3, 1999, pp. 150-164.

MacDonald, Alexander J.R., et al., "The Discovery of Transcutaneous Spinal Electroanalgesia and Its Relief of Chronic Pain," Physiotherapy, vol. 81, No. 11, Nov. 1995, pp. 653-661.

Mediati, R.D., Powerpoint entitled "Mechanisms of Spinal Cord Stimulation," Florence, Oct. 2, 2002, 31 pages.

Melzack, Ronald, et al., "Pain Mechanisms: A New Theory," Science, vol. 150, No. 3699, Nov. 19, 1965, pp. 971-979.

Miles, J D, et al., "Effects of Ramped Amplitude Waveforms on the Onset Response of High-Frequency Mammalian Nerve Block," Journal of Neural Engineering, IOP Publishing, 4, 2007, pp. 390-398.

Muller, A., et al., "Reversible Blockierung der Erregungsleitung im Nerven Dureh Mittelfreimenz-Dauerstrom," Helvetica Physiologica et Pharmacologica Acta, Schwabe & Co., Basel, vol. 25, 1, 1967, pp. 211-213.

Nashold, Blaine S., Jr., M.D., et al., "Dorsal Column Stimulation for Control of Pain," Journal of Neurosurgery, vol. 36, May 1972, pp. 590-597.

North, Richard B., M.D., et al., "Failed Back Surgery Syndrome: 5-Year Follow-Up After Spinal Cord Stimulator Implantation," Neurosurgery Official Journal of the Congress of Neurological Surgeons, Williams & Wilkins, vol. 28, No. 5, May 1991, pp. 692-699.

North, Richard B., M.D., et al., "Spinal Cord Stimulation for Axial Low Back Pain—A Prospective, Controlled Trial Comparing Dual with Single Percutaneous Electrodes," SPINE, Williams and Wilkins, Inc., vol. 30, No. 12, 2003, pp. 1412-1418.

North, Richard B., M.D., et al., "Spinal Cord Stimulation for Chronic, Intratable Pain: Experience Over Two Decades," Neurosurgery, vol. 32, No. 3, Mar. 1993, pp. 384-395.

North, Richard B., M.D., et al., "Spinal Cord Stimulation With Interleaved Pulses: A Randomized, Controlled Trial," Neuromodulation: Technology at the Neural Interface, vol. 10, No. 4, 2007, pp. 349-357.

Perruchoud, Christophe, M.D., et al., "Analgesic Efficacy of High-Frequency Spinal Cord Stimulation: A Randomized Double-Blind Placebo-Controlled Study," International Neuromodulation Society, Neuromodulation: Technology at the Neural Interface, vol. 16, 2013, pp. 363-369.

U.S. Appl. No. 60/895,061, filed Mar. 15, 2007 titled "Spinal Cord Stimulation to Treat Pain.".

"Reversible Blocking of Nerve Conduction by Alternating-Current Excitation," Nature, vol. 185, No. 4842, Aug. 18, 1962, pp. 712-713.

Shealy, C. Norman, M.D., et al., "Electrical Inhibition of Pain by Stimulation of the Dorsal Columns: Preliminary Clinical Report," Anesthesia and Analgesia . . . Current Researches, vol. 46, No. 4, Jul.-Aug. 1967, pp. 489-491.

Shelden, C. Hunter, M.D., et al., "Development and Clinical Capabilities of a New Implantable Biostimulator," The American Journal of Surgery, vol. 124, Aug. 1972, pp. 212-217.

Simpson, B.A., "Spinal Cord Stimulation in 60 Cases of Intractable Pain," Journal of Neurology, Neurosurgery, and Psychiatry, 54, 1991, pp. 196-199.

Simpson, B.A., "Spinal Cord Stimulation," British Journal of Neurosurgery, vol. 11, No. 1, 1997, pp. 5-11.

Smith, Joseph R., et al., "Alleviation of Deafferentation Pain by Posterior Spinal Cord Stimulation Without Development of Paresthesias in the Area of Pain," The Clinical Journal of Pain, 4:157-160, 1988, Raven Press, Ltd., New York, pp. 157-160.

Solomonow, M., Ph.D., et al., "Control of Muscle Contractile Force Through Indirect High-Frequency Stimulation," The Williams & Wilkins Co., American Journal of Physical Medicine, vol. 62, No. 2, 1983, pp. 71-82.

Sweet, William H., M.D., D.Sc., et al., "Stimulation of the Posterior Columns of the Spinal Cord for Pain Control: Indications, Technique, and Results," The Congress of Neurological Surgeons, Clinical Neurosurgery, Honolulu, Hawaii, 1973, Chapter 24, pp. 278-310.

Towell, A.D., et al., "High Frequency Non-Invasive Stimulation Over the Spine: Effects on Mood and Mechanical Pain Tolerance in Normal Subjects," Rapid Science Publishers, Behavioural Neurology, vol. 10, 1997, pp. 61-65.

Urban, Bruno J., M.D., et al., "Percutaneous Epidural Stimulation of the Spinal Cord for Relief of Pain," Journal of Neurosurgery, vol. 48, No. 3, Mar. 1978, pp. 323-328.

Van Den Honert, Christopher, et al., "A Technique for Collision Block of Peripheral Nerve: Frequency Dependence," IEEE Transactions on Biomedical Engineering, vol. BME-28, No. 5, May 1981, pp. 379-382.

Van Den Honert, Christopher, et al., "Generation of Unidirectionally Propagated Action Potentials in a Peripheral Nerve by Brief Stimuli," Science, vol. 206, Dec. 14, 1979, pp. 1311-1312.

Zhang, Xa, et al., "Simulation Analysis of Conduction Block in Myelinated Axons Induced by High-Frequency Biphasic Rectangular Pulses," IEEE Transactions on Biomedical Engineering, vol. 53, No. 7, Jul. 2006, pp. 1433-1436.

* cited by examiner

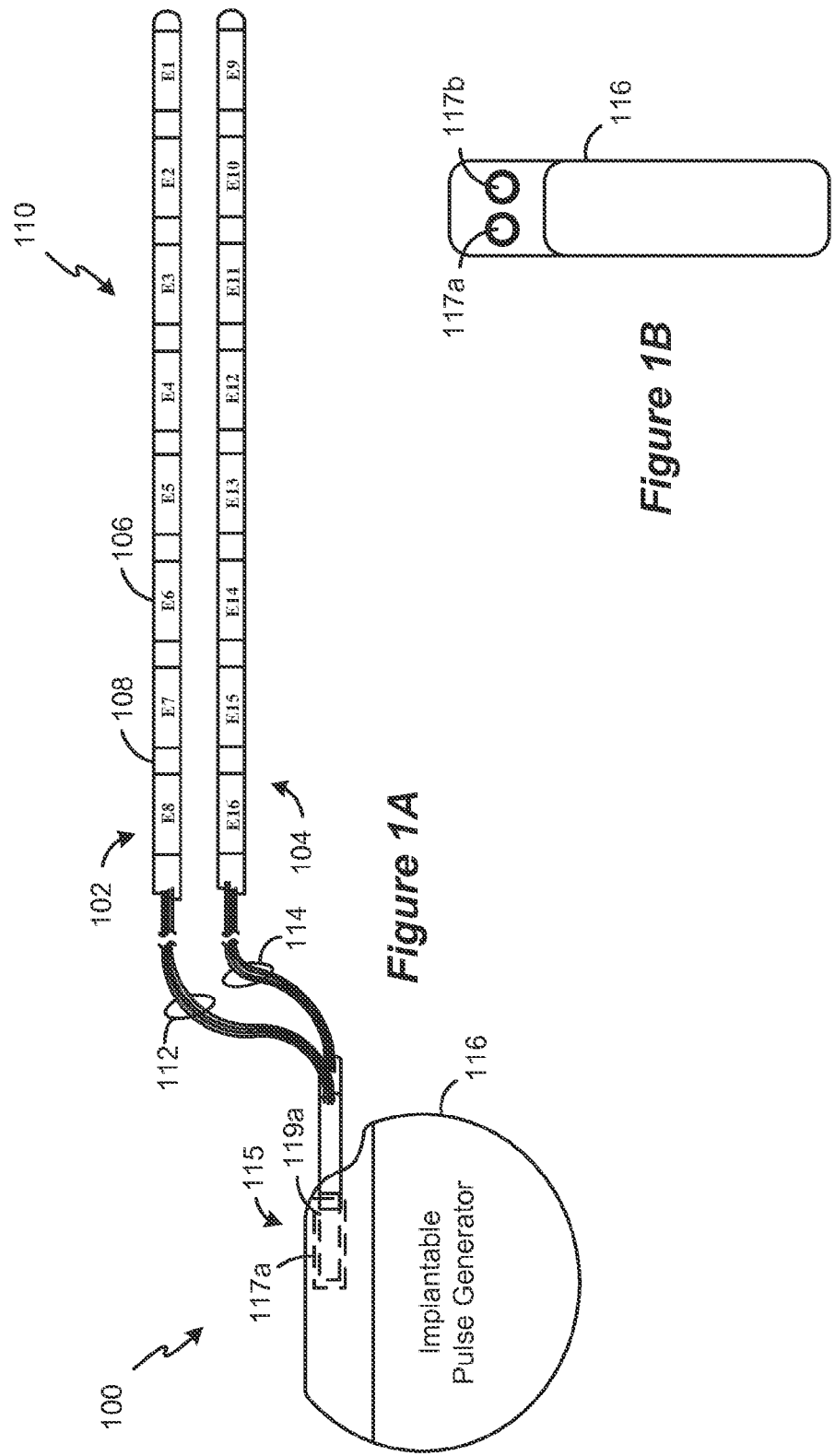
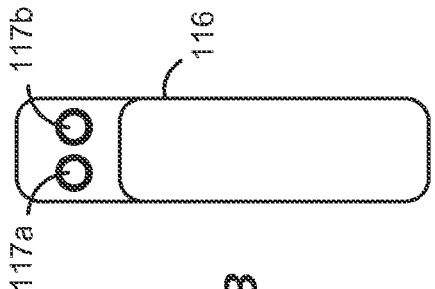
Figure 1A
Figure 1B

FRACTIONALIZED STIMULATION PULSES IN AN IMPLANTABLE STIMULATOR DEVICE

CROSS-REFERENCE TO RELATED APPLICATIONS

This is a continuation of U.S. patent application Ser. No. 12/824,663, filed Jun. 28, 2010, now U.S. Pat. No. 8,812,131 which was a continuation of U.S. patent application Ser. No. 12/121,281, filed May 15, 2008 (now U.S. Pat. No. 7,890,182). The applications are incorporated herein by reference in their entireties and priority is claimed to them.

FIELD OF THE INVENTION

The present invention relates to therapeutic electrical stimulation systems and methods and, more specifically, relates to adjusting electrodes of an implantable stimulator device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a spinal cord stimulation system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A, 1B, 2A, and 2B, a Spinal Cord Stimulation (SCS) system typically includes an Implantable Pulse Generator (IPG) or Radio-Frequency (RF) transmitter and receiver 100 (collectively, "IPGs"), at least one electrode lead 102 and/or 104 having a plurality of electrodes 106, and, optionally, at least one electrode lead extension 120. The electrodes 106 are arranged in a desired pattern and spacing on the lead(s) 102, 104 to create an electrode array 110. Wires 112, 114 within one or more leads(s) 102, 104 connect each electrode 106 in the array 110 with appropriate current source/sink circuitry in the IPG 100.

In an SCS application, the electrodes lead(s) 102, 104 with the electrodes 106 are typically implanted along the spinal cord 19 (FIG. 2B), and the IPG 100 generates electrical pulses that are delivered through the electrodes 106 to the nerve fibers within the spinal column. The IPG 100 body itself is normally implanted in a subcutaneous pocket, for example, in the patient's buttocks or abdomen. The electrode lead(s) 102, 104 exit the spinal column and generally attach to one or more electrode lead extensions 120 (FIG. 2), which in turn are typically tunneled around the torso of the patient to the subcutaneous pocket where the IPG 100 is implanted. Alternatively, if the distance between the lead(s) 102, 104 and the IPG 100 is short, the electrode lead(s) 102, 104 may directly connect with the IPG 100 without lead extensions 120. For examples of other SCS systems and other stimulation system, see U.S. Pat. Nos. 3,646,940 and 3,822,708, which are hereby incorporated by reference in their entireties. Of course, an IPG 100 is an active device requiring energy for operation, which may be provided by an implanted battery or an external power source.

Precise placement of the lead(s) 102, 104 relative to the target nerves is important for achieving a satisfactory physiological response, and for keeping stimulation thresholds low to conserve battery power. A conventional lead implantation procedure commonly places the leads 102, 104 parallel to the spinal cord column 19 at or near the physiological midline 91, as is shown in FIGS. 3A and 3B. More particularly, and as best shown in the cross section of FIG. 3B, the electrode leads 102, 104 are placed directly on the dura mater 51 within the epidural space 70. (Cerebro-spinal fluid 72 is between the electrode array 110 and the white matter 52 of the spinal cord 19. Dorsal root nerves 50 are shown emanating from grey matter 53). When the leads 102, 104 are placed on opposite sides of the physiological midline 91 as shown, additional flexibility is provided in the ability to recruit (i.e., stimulate) nerves in the dorsal column, and to treat symptoms manifesting on either the left or right sides of the patient's body.

In addition to precise placement of the electrode array, proper selection of the electrodes, i.e., determining which of the electrodes 106 in the array should be active in a given patient, is critical for achieving effective stimulation therapy. However, because of the uncertainties of the distances of the electrodes from the neural target, the unknown nature of the specific conductive environment in which the electrode is placed, etc., it generally cannot be known in advance and with precision which combination of active electrodes will be perceived by a patient as providing optimal therapy. As a result, patient therapy generally requires that various electrode combinations be tried and feedback received from the patient as to which of the combinations feels most effective from a qualitative standpoint.

Various electrode combinations and other stimulation parameters can be tried during initialization by programming the IPG 100 using an external wireless clinician or hand-held controller. (Details concerning such controllers can be found in U.S. Patent Publication 2007/0239228, published Oct. 11, 2007, which is assigned to the present application and which is incorporated herein by reference in its entirety). For example, and as best visualized in FIG. 3A, the IPG 100 can be programmed such that electrode E1 comprises an anode (source of current), while E2 comprises a cathode (sink of current). Or, the IPG 100 can be programmed such that electrode E1 comprises an anode, while E9 comprises a cathode. Alternatively, more than one electrode can be used in both the sourcing and sinking of current. For example, electrode E1 could comprise an anode, while both E2 and E9 can comprise cathodes. The amount of current sourced or sunk can also be programmed into the IPG 100. Thus, in the last example, electrode E1 could sink 5 mA, while electrode E2 sources 4 mA and electrode E9 sources 1 mA. The frequency of electrode stimulation pulses, as well as the pulsewidth or duration of such stimulation pulses, is also programmable. As disclosed in the incorporated '228 Publication, the time of no stimulation between pulses is preferably greater than or equal to 3 milliseconds. See '228 Publication, ¶ 65.

Ultimately, which electrodes are activated by the IPG 100, and the polarities (cathode v. anode), magnitudes (amount of current), and frequencies of those activated electrodes, are based largely on patient feedback during IPG initialization as noted earlier. Thus, the patient, perhaps assisted by a clinician, will experiment with the various electrode settings, and will report relative levels of comfort and therapeutic effectiveness to arrive at electrode settings that are best for a given patient's therapy.

In the prior art, patients and/or clinicians used a technique called "field steering" or "current steering" to try and simplify the iterative process for determining a patient's optimal electrode settings during initialization of the IPG. See, e.g., U.S. Pat. No. 6,909,917, which is incorporated herein by reference in its entirety. In current steering, the current sourced or sunk by the electrodes is gradually redistributed by the patient or clinician to different electrodes using a single stimulation timing channel. Such steering can be facilitated using some sort of user interface associated with the external controller, such as a joystick or other directional device. Simple examples of current steering are shown in FIGS. 4A, 4B, and 5. Starting first with FIG. 4A, assume that the IPG 100 has an initial condition, namely that electrode E1 has been programmed to sink 10 mA of current, while electrode E3 has been programmed to source 10 mA of current. This initial condition might be arrived at after some degree of experimentation, and might be a condition at which the patient is feeling a relatively good response, but a response which has not yet been fully optimized.

In an attempt at further optimization, current steering can commence from these initial conditions. Assume that optimization by current steering will ultimately arrive at the final condition of FIG. 4B. As shown, this final condition sinks 10 mA at electrode E2. Thus, during current steering, 10 mA of sink current is moved from E1 (the initial condition) to E2 (the final condition). To do this, electrode E1 is selected and the current sunk from that electrode is moved downward, for example, by clicking downward on the controller's joystick. As shown in FIG. 5, this moves some increment of sinking current (as illustrated, a 2 mA increment) from electrode E1 to electrode E2, such that E1 now sinks 8 mA and E2 sinks 2 mA. Another downward click moves another 2 mA, so that now E1 sinks 6 mA and E2 sinks 4 mA, etc., until the full 10 mA is moved to E2 as per the final condition.

Gradual steering of the current in increments is generally considered advisable to safeguard against abrupt changes of the stimulation field which may be uncomfortable or dangerous for the patient. Abrupt shifting of the entirety of the current from one electrode to another could have unforeseen and undesirable effects. Different nerves are affected by such a change in electrode activation, and it is not necessarily known how moving a full allotment of current would affect those nerves. If the current when applied to the new electrodes (e.g., from E1 to E2) is too low (i.e., sub-threshold), no clinical response would be noticed, even if the electrodes were ultimately suitable choices. If the current is too high (i.e., supra-threshold), the result might be painful (or dangerous) for the patient. Accordingly, incremental movement of the current is considered a good approach.

However, the illustrated current steering approach requires two different electrodes (e.g., E1 and E2) to simultaneously act as current sinks during the intermediate steering steps. This can be an implementation problem in IPG architectures that don't allow the simultaneous selection of two or more electrodes to act as the source or sink. For example, some simpler IPG architectures may provide only a single current source circuit and a single current sink circuit, which circuits can only be coupled to one electrode at a time. Because such architectures will not support simultaneous activation of two or more electrodes as sinks or sources, the current steering approach of FIG. 5 can't be used.

Other current steering approaches provide additional complexities. For example, the current steering approach illustrated in FIG. 6 is disclosed in U.S. Patent Publication 2007/0239228, which was incorporated by reference above. In this approach, steering of the current from one electrode to another occurs by establishing the steered current in a second timing channel. (Because the operation of timing channels are explained in detail in the '228 publication, they are not further explained here). Thus, and as shown, current in the transferring electrode (E1) is initially established in a first timing channel 'A.' As the current is incrementally steered to receiving electrode E2, that steered current forms in a second timing channel 'B,' such that the pulses in timing channel A and B are non-overlapping. The result after several incremental transfers of current is the final condition in which the sink current resides entirely with electrode E2 is in the second timing channel B.

This approach of the '228 publication thus requires IPG hardware and software necessary to support different timing channels. Not all IPGs will have such hardware or software, and so will be unable to benefit from the current steering technique of FIG. 6. Even in those IPGs that can support multiple timing channels, such a current steering technique is relatively complex, and is potentially limited. For example, although not shown in FIG. 6, one skilled in the art will understand that the pulses must generally be followed by either a passive or active current recovery period. Because pulses in the next timing channel cannot be executed until currently recovery of the pulses in the preceding timing channel is completed, the ability to use the '228 publication's current steering technique is not guaranteed. For example, if the stimulation pulses are of long duration or of a high frequency, there may simply not be enough time in which to interleave the pulses in the two timing channels, especially when current recovery periods are considered.

Accordingly, what is needed is an improved method for optimizing electrode activation during the set up of an implantable stimulator device, and this disclosure provides embodiments of such a solution.

BRIEF DESCRIPTION OF THE DRAWINGS

FIGS. 1A and 1B show an electrode array and the manner in which it is coupled to the implantable stimulator device in a SCS.

DETAILED DESCRIPTION

The description that follows relates to use of the invention within a spinal cord stimulation (SCS) system. However, the invention is not so limited. Rather, the invention may be used with any type of implantable medical device system. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

A method for configuring stimulation pulses in an implantable stimulator device having a plurality of electrodes is disclosed, which method is particularly useful in adjusting the electrodes by current steering during initialization of the device. In one aspect, a set of ideal pulses for patient therapy is determined, in which at least two of the ideal pulses are of the same polarity and are intended to be simultaneously applied to corresponding electrodes on the implantable stimulator device during an initial duration. These pulses are reconstructed into fractionalized pulses, each comprised of pulse portions. The fractionalized pulses are applied to the corresponding electrodes on the device during a final duration, but the pulse portions of the fractionalized pulses are not simultaneously applied during the final duration.

Figures 2A, 2B:
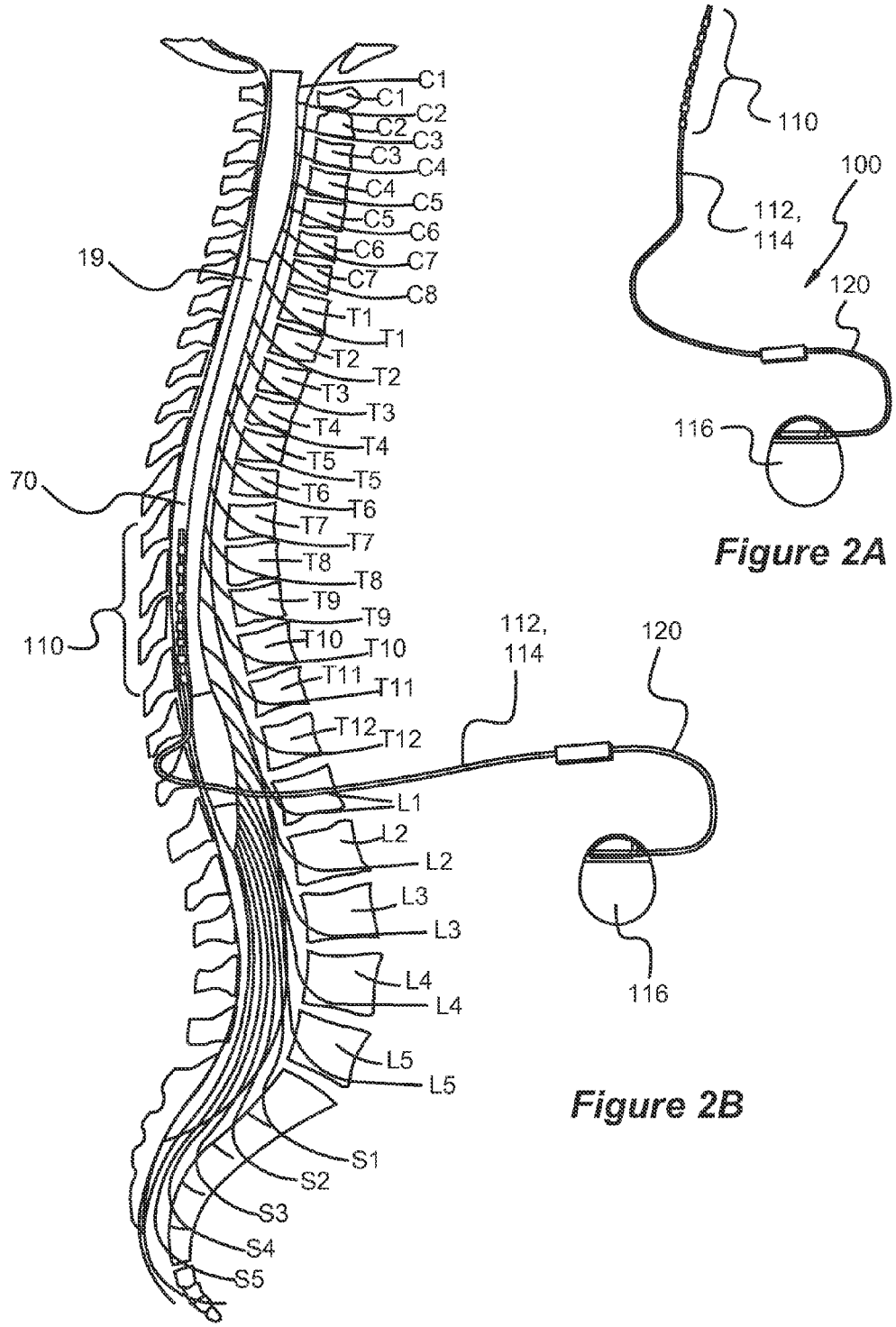
FIGS. 2A and 2B show a placement of the percutaneous lead for spinal cord stimulation with an in-line electrode array inserted alongside the spinal cord in the epidural space, in close proximity to the dura mater.
Figure 3A:
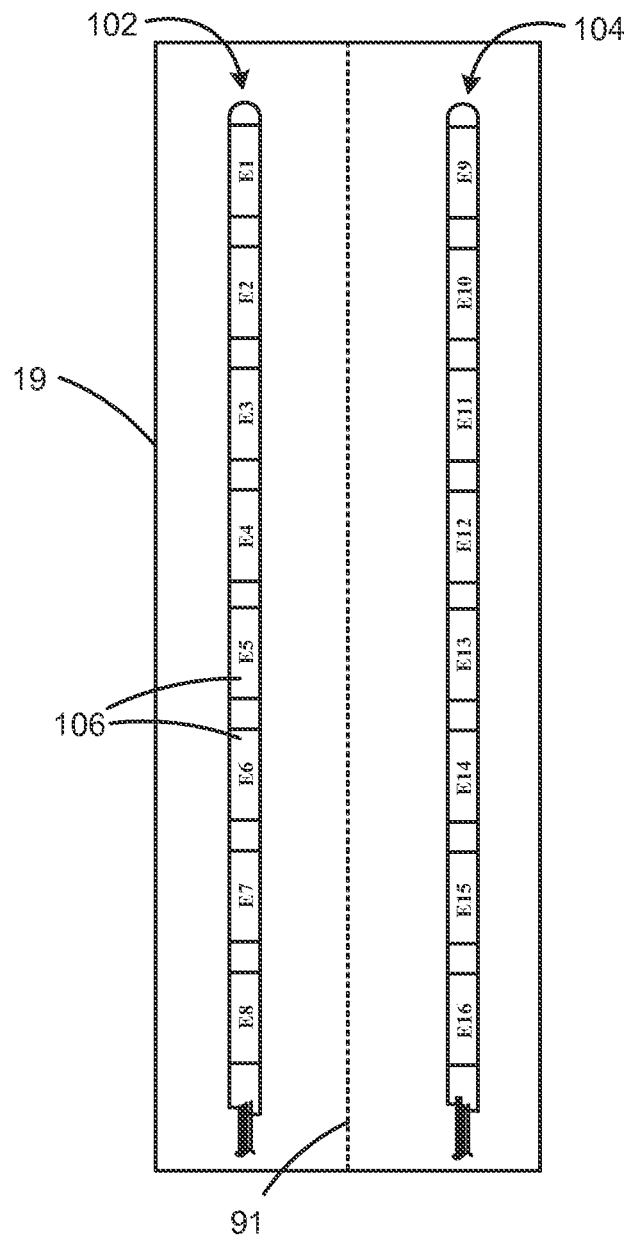
FIGS. 3A and 3B show placement of two in-line electrode arrays on the left and right sides of the physiological midline of the spinal cord, respectively, in a perspective view and in cross-section.
Figure 3B:
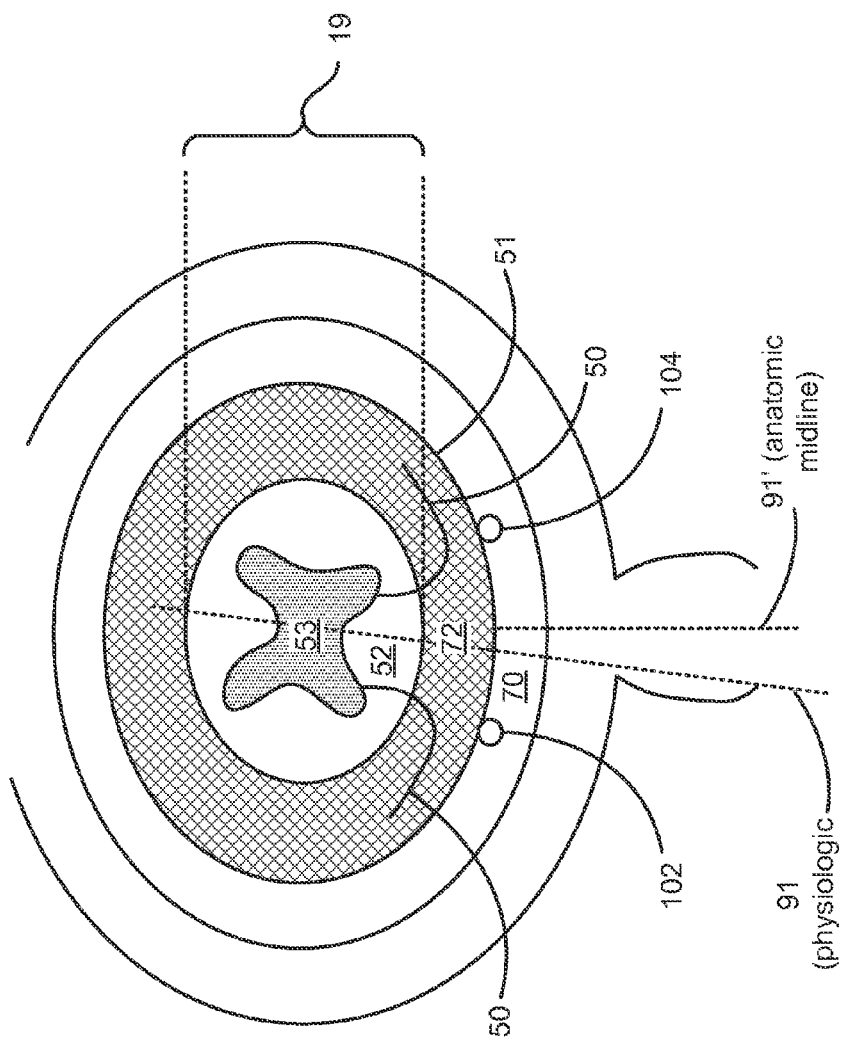
Figures 4A, 4B:
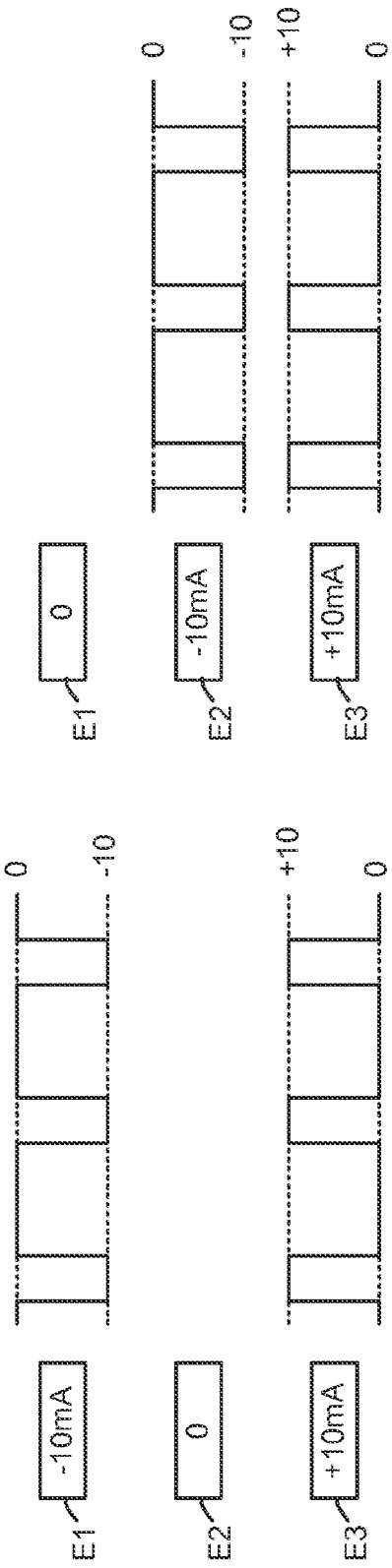
FIGS. 4A, 4B and 5 show an electrode current steering technique of the prior art.
Figure 5:
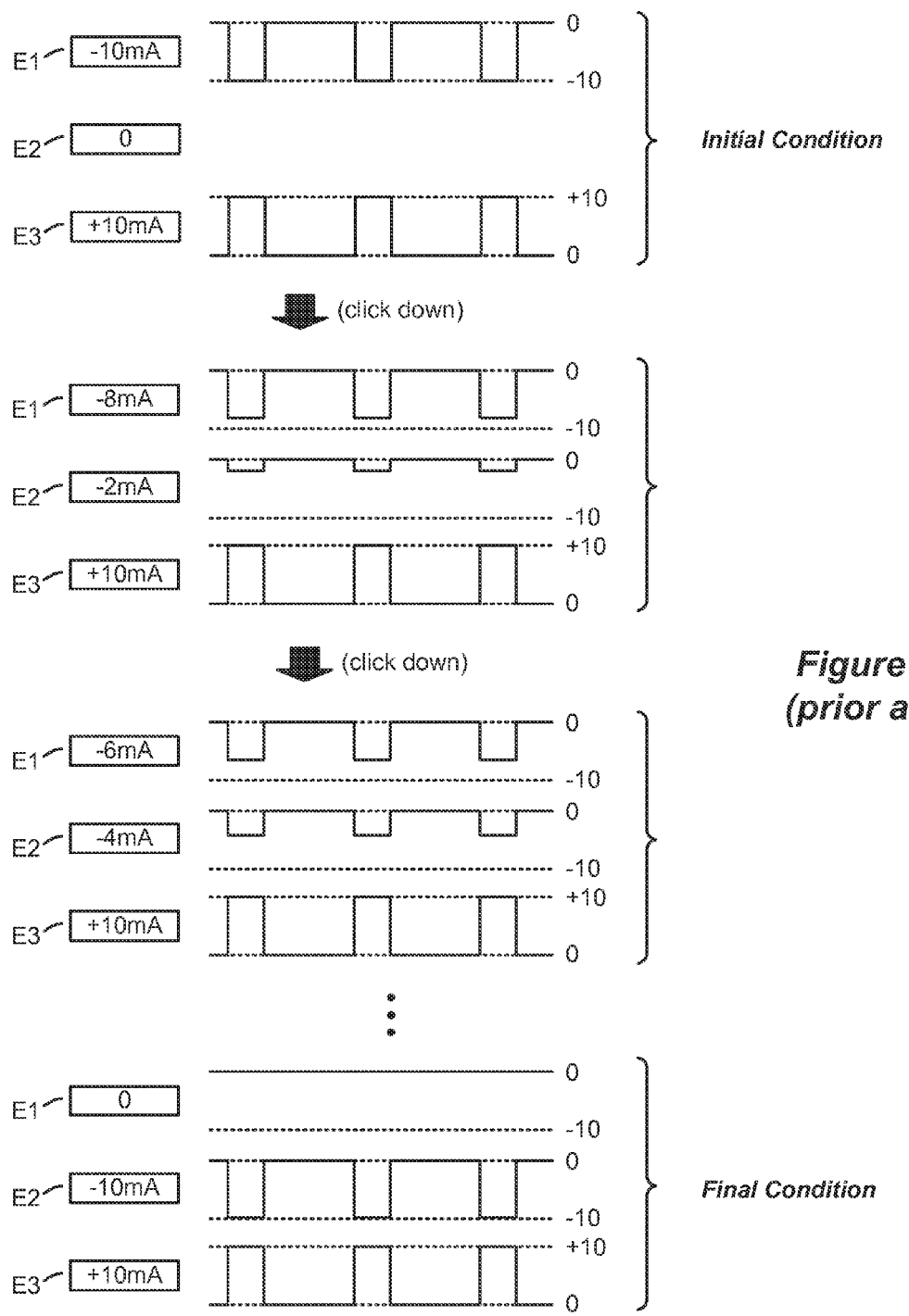
Figure 6:
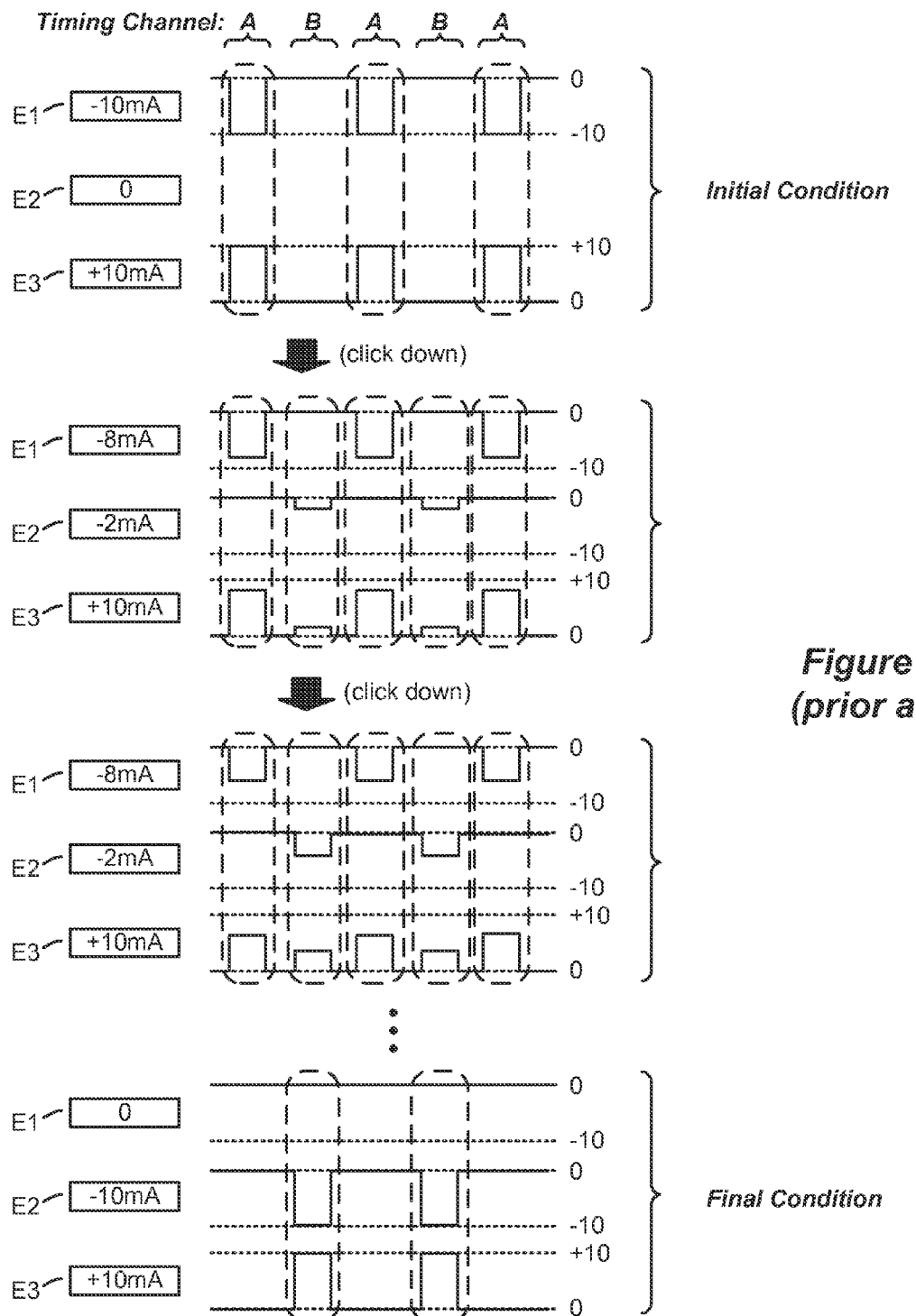
FIG. 6 shows another electrode current steering technique of the prior art.
Figure 7A:
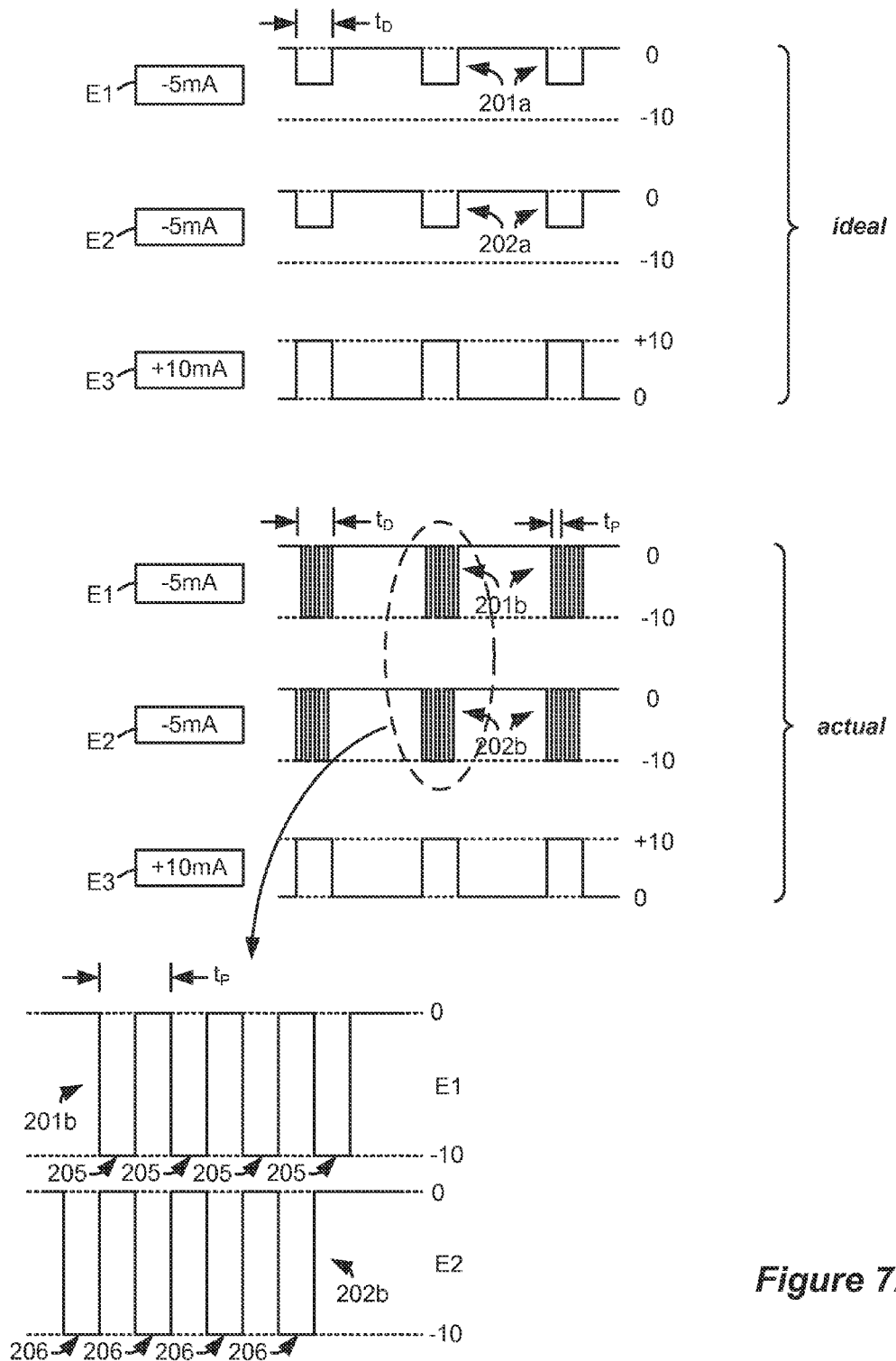
FIGS. 7A and 7B show how ideally simultaneous pulses can be reconstructed as non-simultaneous fractionalized pulse portions in accordance with an embodiment of the disclosed technique.
Figure 7B:
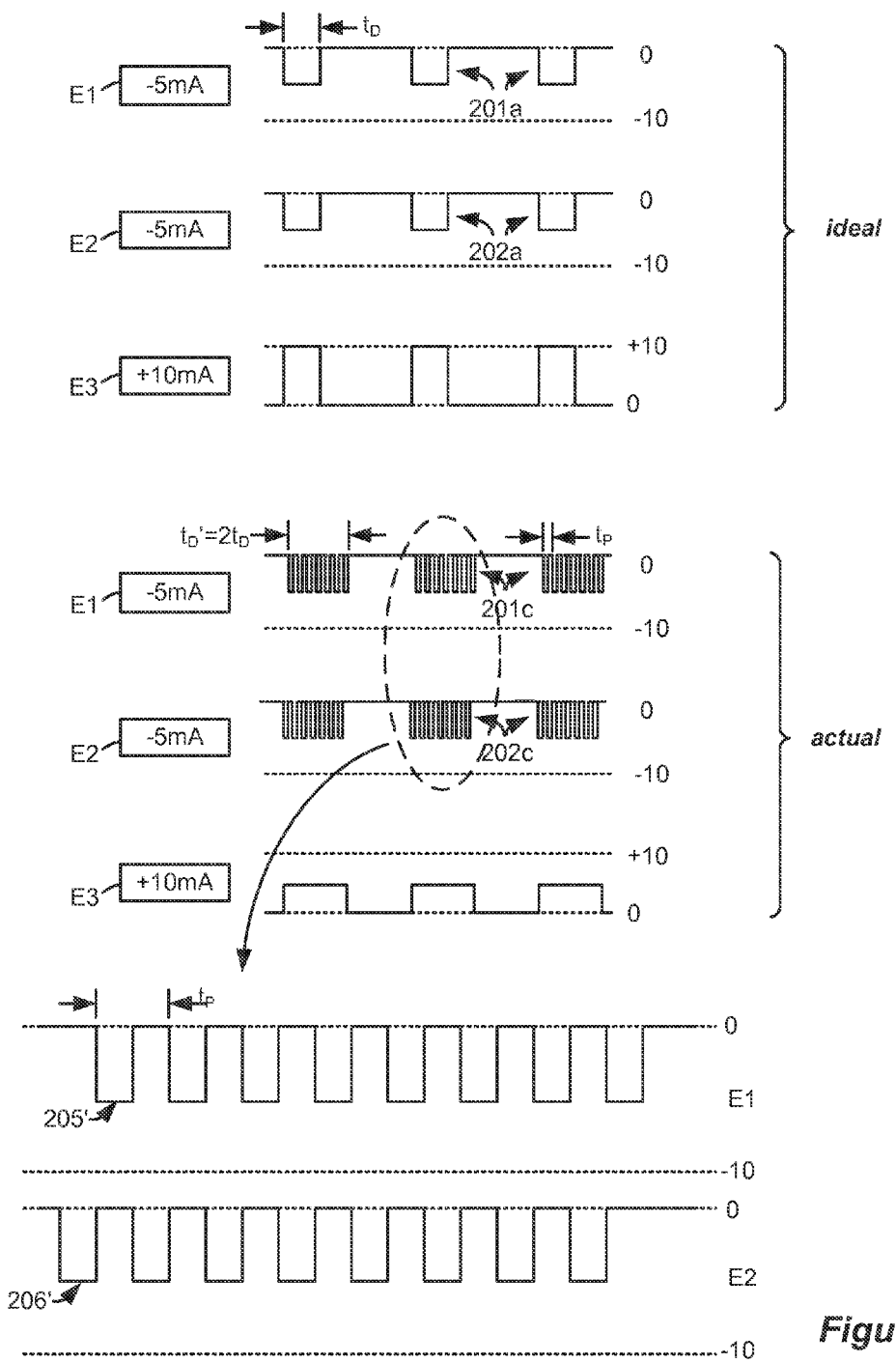
Figures 8A, 8B:
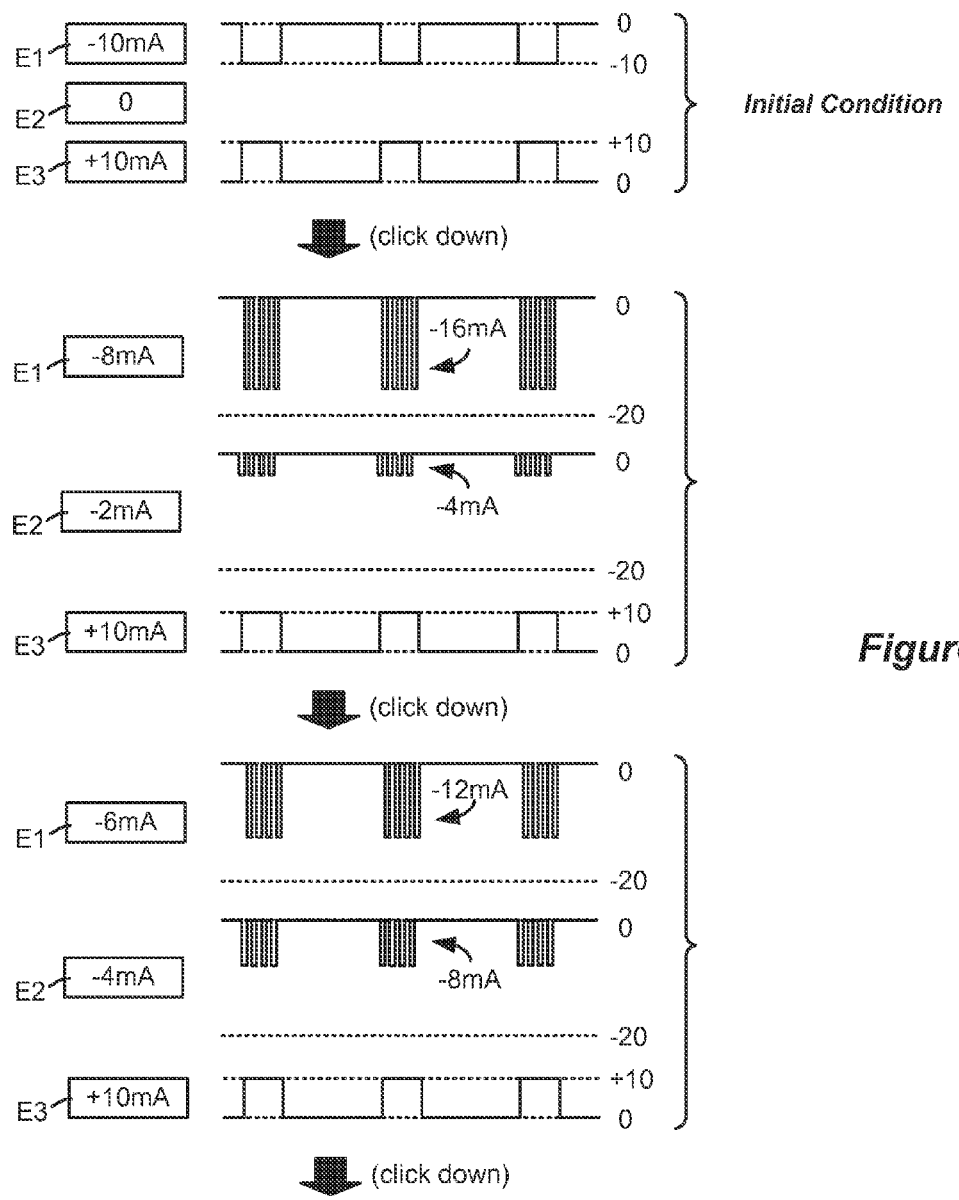
FIGS. 8A and 8B show how the fractionalized pulse portions can be used in a current steering application.
Figure 7A:
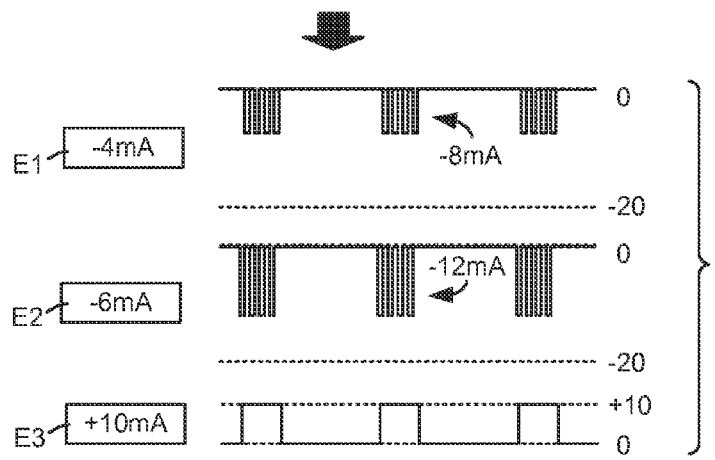
Figure 7A:
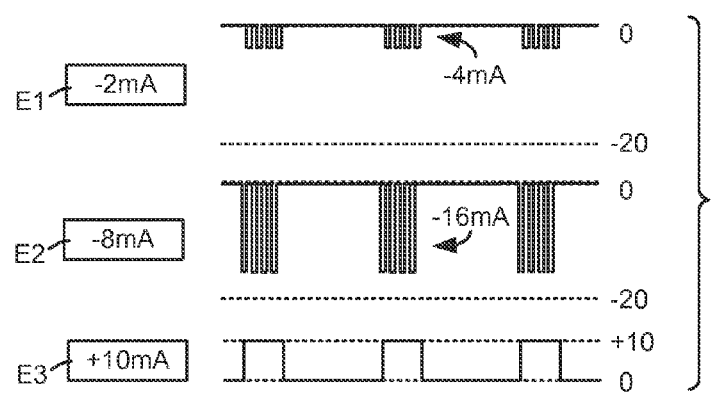
Figure 8B:
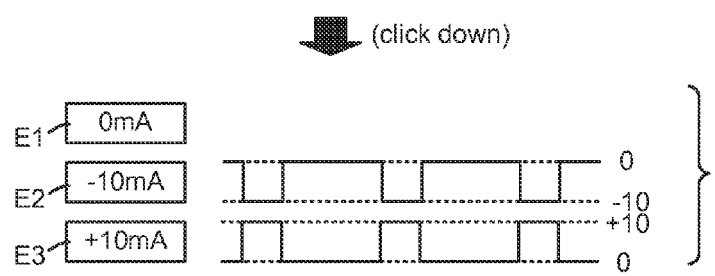

An improved current steering technique for an implantable stimulator device is illustrated in FIGS. 8A and 8B. However, before discussion of that technique, a more fundamental understanding of the technological and biological aspects of the technique are illustrated in FIGS. 7A and 7B.

FIG. 7A illustrates an intermediary set of pulses as might be desired during current steering. As shown, electrodes E1 and E2 are desired to be simultaneously asserted as pulses 201a and 202a, each providing a 5 mA sink. This condition of simultaneity could be encountered when transferring sink current from E1 to E2, as was illustrated earlier.

The actual implementation of such idealized pulses according to an aspect of the invention comprises a reconstruction of these ideal pulses 201a and 202a as fractionalized pulses 201b and 202b which are not simultaneous. As can be seen in the magnified illustration at the bottom of FIG. 7A, only one fractionalized pulse portion 205 or 206 is asserted at any given time. As such, the fractionalized pulse portions 205 and 206 are interleaved.

The frequency of the fractionalized pulse portions 205, 206 in the illustrated example equals $1/t_P$, where $t_P$ comprises the pulse portion period. Because the pulse portion period $t_P$ is generally much shorter than the duration of the ideal pulses, $t_D$, there would typically be many fractional pulse portions 205 or 206 occurring within duration $t_D$, although only a few such portions are shown in FIG. 7A for ease of illustration.

Stimulation using fractionalized pulses 201b and 202b causes recruited neurons to react to the pulse portions 205 and 206 in an additive manner. For example, for a depolarizing sequence, the transmembrane potential will slowly depolarize on average with each additional pulse portion. The sequence of pulse portions 205 and 206 takes advantage of the non-linear membrane dynamics which tend to move a recruited neuron towards depolarization. In particular, short pulse portions will tend to open the "m" gates of the sodium channels. As the gates open, the cell membrane will tend to depolarize slightly more. A combination of pulse portions can then depolarize the membrane enough until, as with the ideal pulses 201a and 202a, an action potential is generated in the recruited neurons. In other words, the nerves recruited by the electrodes E1 and E2 will receive effective therapy even though the fractionalized pulses 201b and 202b are interrupted and non-simultaneous unlike their ideal counterparts 201a and 202a.

The pulse portion period, $t_P$ (frequency $1/t_P$), may be kept lower than the chronaxie time, which is approximately 100 to 150 microseconds or so (i.e., 10000 to 6666.7 Hz frequency). However $t_P$ can also exceed the chronaxie time, although in such an application higher energies (e.g., pulse portion amplitudes) might be required as explained further below. However, effectiveness in therapy, even with increasing energies, would be expected to diminish when $t_P$ exceeds 500 microseconds or so (i.e., lower than 2000 Hz).

In the illustrated example, the fractionalized pulse portions 205 and 206 have a duty cycle of approximately 50%, such that only one pulse portion 205 or 206 from fractionalized pulses 201b and 202b are asserted at any given time. Note also that the amplitude of those pulse portions 205, 206 (−10 mA) are twice what is called for in the corresponding ideal pulses 201a and 201b (−5 mA). This amplitude relates to the duty cycle of the pulse portions, and stems from the recognition that the total amount of injected charge remains an important first-order variable in effective patient therapy. Thus, when one compares the ideal pulses 201a and 202a with their fractionized actual counterparts 202a and 202b, the amount of charge (i.e., the area under their curves) is same. So, if the duty cycle of the fractionalized portions are 50%, an amplitude of twice would be indicated; if the duty cycle is 33.3% (as might occur should three electrodes need to act as either a source or sink at one time), three times the amplitude would be indicated, etc.

However, it is not strictly required that the amount of charge in the ideal and fractionalized pulses be equal, and in a given application amplitudes of the fractionalized pulse portions 205 and 206 may need to be adjusted to provide slightly more or less charge than the injected charge of the ideal pulses 201a and 202a. In one example, and as alluded to above, longer pulse portion periods might require higher amounts of charge than are represented by their ideal counterparts. For example, assuming a 50% duty cycle and a pulse portion period $t_P$ slightly above the chronaxie time, the amplitude of the fractionalized pulse portions 205 and 206 may be higher than double (e.g., 2.1 times) the amplitude of the corresponding ideal pulses 201a and 202a, resulting in a higher amount of charge. If $t_P$ is made even larger, than the amplitude of the fractionalized pulses portions could increase even further (e.g., to 2.2 times), etc.

Because of the increase in amplitude of the fractionalized pulse portions 205, 206, the current generation circuitry in the IPG 100 must be capable of sustaining higher compliance voltages. See U.S. Published Patent Application 2007/0097719, published May 3, 2007, which is incorporated herein in its entirety, for a further discussion of compliance voltage generation in IPGs.

FIG. 7B illustrates another way in which simultaneous pulses can be reconstructed in accordance with the invention. As with FIG. 7A, the ideal pulses 201a and 201b are fractionalized and interleaved as shown at 201c and 202c. However, the fractionalized pulse portions 205' and 206' have the same amplitude (−5 mA) as do their ideal pulse counterparts, but the fractionalized pulses 201c and 202c have a duration $t_D'$ of twice the duration $t_D$ of the ideal pulses. The result, as with FIG. 7A, is ideal and fractionalized pulses that are comprised of approximately the same amount of charge. While the reconstruction method of FIG. 7B does modify the duration of the ideal pulses (i.e., from $t_D$ to $t_D'$), such pulse duration modification only affects patient therapy as a second-order variable; the more-important first-order variable of total charge remains essentially unchanged, and so patient therapy is not significantly impacted by the change in duration. Of course, assuming that the amount of charge is kept approximately the same, other durations, both longer and shorter than the duration of the ideal pulses, can be used in the actual fractionalized pulses. The two-fold duration increase shown in FIG. 7B is therefore merely exemplary.

The system may use both techniques—higher pulse amplitude (FIG. 7A) or higher pulse duration (FIG. 7B)—as convenient. For example, the logic in the IPG 100 may choose an appropriate pulse fractionalization strategy that saves energy. Or, the logic in the IPG 100 may choose fractionalization parameters to prevent saturation of the output—e.g., if the amplitude has been maximized then the pulse width or duration is increased, etc.

There are significant benefits to reconstructing the ideal pulses as fractionalized pulses as shown in FIGS. 7A and 7B. Even though the patient's nerves biologically sense simultaneous stimulation, the reality is that no more than one electrode is truly active as a source or sink at any given time, given the interleaved fractionalized pulse portions 205 and 206. Therefore, this technique, and the steering technique described subsequently in FIGS. 8A and 8B, can be implemented in IPGs having simpler architectures in which source or sink circuitry is coupleable to only a single electrode at a time.

In an actual implementation, there would be some set-up time necessary to switch current sink circuitry from E1 to E2, and so the duty cycles of the fractionalized pulse portions 205 and 206 may be less than an ideal 50% for example. However, such set-up time would be relatively short compared to the pulse portion period $t_P$, and so such set-up time is negligible and therefore not illustrated in the figures. For example, it may take only a few 0.1 of a microsecond to switch the current from one electrode to another, i.e., from a pulse portion 205 to a pulse portion 206. However, one skilled in the art will realize that the transition times and other non-idealities will mean that the actual charge of the fractionalized pulses may only approximate the charge specified by the ideal pulses.

FIGS. 8A and 8B illustrate how the reconfigured fractionalized pulses can be utilized in an improved current steering scheme. As with FIGS. 5 and 6, FIGS. 8A and 8B illustrate the simple example of gradually steering 10 mA of sink current from electrode E1 to electrode E2. The initial condition at the top of FIG. 8A is defined in a single timing channel, which timing channel specifies the amplitude, duration, and frequency of the ideal stimulation pulses. Starting from that initial condition, a user (patient or clinician) selects to move an increment (e.g., 2 mA) of sink current from E1 to E2, perhaps by a downward click of a joystick on an external controller as mentioned previously. At this point, the logic in the IPG 100 recognizes the need for sink current to be simultaneously present at both E1 (8 mA) and E2 (2 mA). Accordingly, the logic in the IPG reconstructs these ideal pulses as shown in the second condition of FIG. 8A. This second condition reconfigures the pulses as fractionalized pulses. Because these pulses are fractionalized and interleaved, their amplitudes are doubled to (in this example) approximately preserve the desired amount of charge. Thus, the fractionalized pulse portions at E1 (with a duty cycle of approximately 50%), have an amplitude of approximately −16 mA over the same duration as the initial pulses, thus simulating the −8 mA pulse that is desired; the interleaved pulses portions at E2 likewise have an amplitude of approximately −4 mA to simulate the desired −2 mA pulse.

While the logic in the IPG 100 can be programmed to automatically fractionalize the pulses in a predetermined manner when necessary, it should be noted that this is only an embodiment. The decision on how to perform the fractionalization can also be made by a user with a wireless external controller. For example, a user can access a user interface on the external controller to specify fractionalization parameters such as amplitude, duration, period, etc., with such parameters being wirelessly transmitted to the nonvolatile memory storage in the IPG 100. Because external controllers are well known in the art, they are not discussed further.

Effecting such fractionalization is achieved in a preferred embodiment by re-writing the timing channel in which the initial condition was specified. In other words, moving from the initial to the second condition does not require the establishment of a second timing channel, because the logic in the IPG 100 preferably re-writes the first timing channel to add the additional electrode (E2), to specify the duty cycle and period ($t_P$) of the first and second interleaved pulses, etc. This is an improvement over prior art current steering techniques which require the use of steering using additional timing channels, such as the '228 publication referenced earlier. In short, the presently-disclosed current steering technique requires only a single timing channel, making it amenable to IPG architectures having hardware or software capable of handling only a single timing channel. Having said this, it should be recognized that the invention can also be implemented in IPGs having a plurality of timing channels, and so is not limited to single timing channel devices.

As shown further in FIG. 8A, further user selection to steer another increment of current results in decreasing the amplitude of the fractionalize pulse portions at the transmitting electrode E1 (from −16 mA to −12 mA) while concurrently increasing the amplitude of the fractionized pulse portions at the receiving electrode E2 (from −4 mA to −8 mA). Such adjustment merely requires updating the amplitudes in the first (initial) timing channel, and does not require a second timing channel. Continuing selections eventually result in the final desired condition illustrated at the bottom of FIG. 8B, in which the full amount of sink current (−10 mA) is now present entirety at electrode E2. Because this final condition does not require electrode E1 and E2 to both sink current simultaneously, the pulses at E2 can be reconfigured with a 100% duty cycle pulse at its normal amplitude. Again, this happens by re-writing the first timing channel.

It should be understood that reference to an "electrode on the implantable stimulator device" includes electrodes on the implantable stimulator device, or the electrodes on the associated electrode leads, or any other structure for directly or indirectly stimulating tissue.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device (ISD), comprising:
   a memory configured to store a first frequency, wherein the first frequency comprises a stimulation frequency that is considered therapeutically effective for a patient;
   logic configured to define a group of a plurality of pulses, wherein the pulses within the group have a second frequency greater than or equal to 2000 Hz; and
   source or sink circuitry configured to periodically apply the group of the pulses to at least one electrode at the first frequency.

2. The device of claim 1, wherein the pulses within the group have a duty cycle of approximately 50%.

3. The device of claim 1, wherein the second frequency is greater than or equal to 2000 Hz and less than or equal to 10000 Hz.

4. The device of claim 1, further comprising a receiver configured to wirelessly receive the first frequency from a device external to the ISD.

5. The device of claim 4, wherein the first frequency is considered therapeutically effective for a patient by determining the first frequency to be therapeutically effective for a particular patient at the external device.

6. The device of claim 1, further comprising a receiver configured to wirelessly receive from a device external to the ISD a first duration at which the group of the plurality of pulses are configured to be periodically applied by the source or sink circuitry, wherein the memory is further configured to store the first duration.

7. The device of claim 1, wherein the pulses in the group are either only anodic or only cathodic.

8. The device of claim 1, wherein the source or sink circuitry comprises constant current source or sink circuitry configured to periodically apply the group of the pulses to at least one electrode at a constant current.

9. The device of claim 1, further comprising at least one lead, wherein the at least one electrode is carried by the at least one lead.

10. A method for creating pulses in an implantable stimulator device (ISD), comprising:
receiving a first frequency at the ISD, wherein the first frequency comprises a stimulation frequency that is considered therapeutically effective for a patient; and
constructing in the ISD groups of a plurality of pulses that can be applied to at least one electrode of the ISD, wherein the pulses within each group are constructed at a second frequency greater than or equal to 2000 Hz, and wherein the groups are constructed at the first frequency, and wherein the groups of the pulses are constructed in a single timing channel in the ISD.

11. The method of claim 10, wherein the pulses within each group have a duty cycle of approximately 50%.

12. The method of claim 10, wherein the second frequency is greater than or equal to 2000 Hz and less than or equal to 10000 Hz.

13. The method of claim 10, wherein the first frequency is wirelessly received from a device external to the ISD.

14. The method of claim 13, wherein the first frequency is considered therapeutically effective for the patient by further determining that the first frequency is therapeutically effective for the patient at the external device.

15. The method of claim 10, further comprising wirelessly receiving a first duration from a device external to the ISD for each group of the plurality of pulses.

16. The method of claim 15, further comprising determining that the first duration is therapeutically effective for the patient at the external device.

17. The method of claim 10, wherein the pulses in each group are either only anodic or only cathodic.

18. The method of claim 10, wherein the pulses in each group are constructed with a constant current.

19. The method of claim 10, wherein the groups are constructed with a time between successive groups during which the pulses are not applied.

20. A method for providing stimulation to at least one electrode of an implantable stimulator device (ISD) implanted in a patient, comprising:
receiving a first frequency at the ISD, wherein the first frequency comprises a stimulation frequency determined to be therapeutically effective for the patient;
constructing in the ISD a group of a plurality of pulses, wherein the pulses within the group have a second frequency greater than or equal to 2000 Hz; and
periodically applying the group of the pulses to the at least one electrode at the first frequency, wherein the group of the pulses is periodically applied with a time between consecutive applications of the group during which the pulses are not applied.

21. The method of claim 20, wherein the second frequency is greater than or equal to 2000 Hz and less than or equal to 10000 Hz.

22. The method of claim 20, wherein the first frequency is wirelessly received from a device external to the ISD.

23. The method of claim 22, wherein the first frequency is determined to be therapeutically effective for the patient at the external device.

24. The method of claim 20, wherein the pulses in each application of the group are either only anodic or only cathodic, and are applied to the at least one electrode at a constant current.

25. The method of claim 20, wherein the ISD is coupled to first and second leads, and wherein the first and second leads are positioned parallel to the patient's spinal cord.

26. The method of claim 25, wherein the first and second leads are positioned to the right and left of a physiological midline of the patient's spinal cord.

27. The method of claim 25, wherein the first and second leads are positioned within an epidural space of the patient's spinal cord.

28. A method for creating pulses in an implantable stimulator device (ISD), comprising:
receiving a first frequency at the ISD, wherein the first frequency comprises a stimulation frequency that is considered therapeutically effective for a patient; and
constructing in the ISD groups of a plurality of pulses that can be applied to at least one electrode of the ISD, wherein the pulses within each group are constructed at a second frequency greater than or equal to 2000 Hz, and wherein the groups are constructed at the first frequency with a time between successive groups during which the pulses are not applied.

29. The method of claim 28, wherein the pulses within each group have a duty cycle of approximately 50%.

30. The method of claim 28, wherein the second frequency is greater than or equal to 2000 Hz and less than or equal to 10000 Hz.

31. The method of claim 28, wherein the first frequency is wirelessly received from a device external to the ISD.

32. The method of claim 31, wherein the first frequency is considered therapeutically effective for the patient by further determining that the first frequency is therapeutically effective for the patient at the external device.

33. The method of claim 28, further comprising wirelessly receiving a first duration from a device external to the ISD for each group of the plurality of pulses.

34. The method of claim 33, further comprising determining that the first duration is therapeutically effective for the patient at the external device.

35. The method of claim 28, wherein the pulses in each group are either only anodic or only cathodic.

36. The method of claim 28, wherein the pulses in each group are constructed with a constant current.

* * * * *